United States Patent [19]
Johnson et al.

[11] Patent Number: 5,425,714
[45] Date of Patent: Jun. 20, 1995

[54] PERFUSION CATHETER WITH MOVING BODY

[75] Inventors: Kirk L. Johnson, Miami Lakes; Mark N. Inderbitzen, Miramar, both of Fla.

[73] Assignee: Cordis Corporation, Miami Lakes, Fla.

[21] Appl. No.: 212,970

[22] Filed: Mar. 15, 1994

[51] Int. Cl.⁶ .......................................... A61M 29/00
[52] U.S. Cl. ..................................... 604/102; 604/96; 604/280
[58] Field of Search ................ 604/96, 102, 164, 264, 604/280; 606/192, 194

[56] References Cited

U.S. PATENT DOCUMENTS

| | | |
|---|---|---|
| 4,581,017 | 4/1986 | Sahota . |
| 4,723,549 | 2/1988 | Wholey et al. . |
| 4,762,129 | 8/1988 | Bonzel ................................ 604/96 X |
| 4,771,777 | 9/1988 | Horzewski et al. .................. 606/194 |
| 4,820,271 | 4/1989 | Deutsch . |
| 4,944,745 | 7/1990 | Sogard et al. ........................ 606/194 |
| 4,968,306 | 11/1990 | Huss et al. ............................ 604/264 |
| 5,035,694 | 7/1991 | Kasprzyk et al. . |
| 5,063,018 | 11/1991 | Fontirroche et al. . |
| 5,152,277 | 10/1992 | Honda et al. . |
| 5,195,971 | 3/1993 | Sirhan . |
| 5,205,822 | 4/1993 | Johnson et al. . |

*Primary Examiner*—Corrine Maglione
*Attorney, Agent, or Firm*—Gerstman, Ellis & McMillin, Ltd.

[57] ABSTRACT

An intravascular balloon catheter comprises a catheter body having a proximal end a distal end, and a balloon carried adjacent the distal end. The catheter body defines an inflation tube which extends along essentially the length of the body proximal to the balloon and which communicates with the interior of the balloon. The catheter body also defines a lumen having an open, distal end and extending at least most of the length of the body. A first tube, aligned with the lumen, extends through the balloon and is open at both ends. A portion of the catheter which defines the lumen is longitudinally slidable relative to the balloon and the first tube between an advanced position and a retracted position. In the advanced position the lumen and first tube are together to allow advancement of a guidewire through both the lumen and the first tube. In the retracted position, the lumen is spaced from the first tube, so that the first tube is open to receive blood flow therethrough.

7 Claims, 1 Drawing Sheet

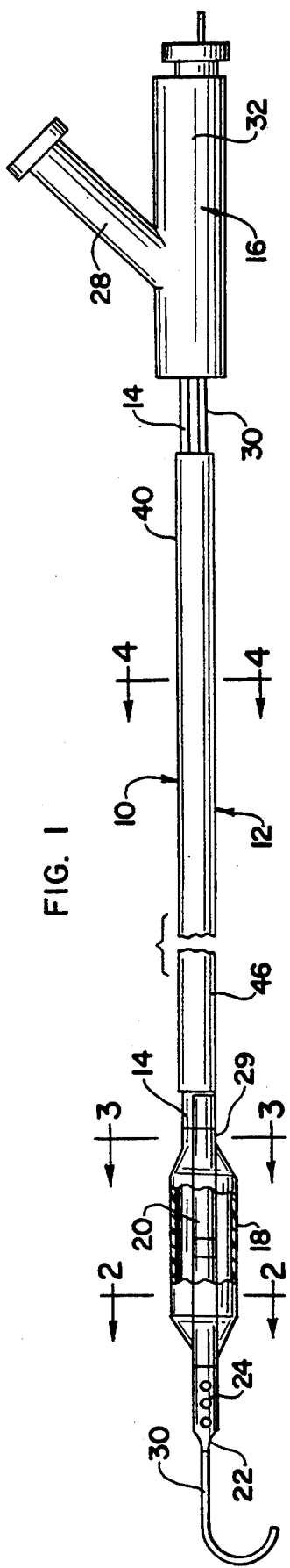
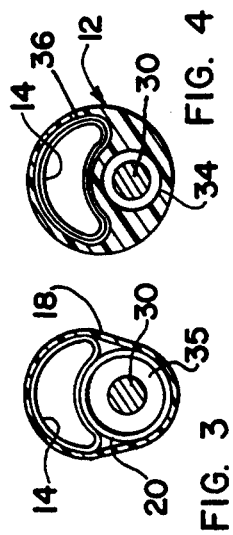
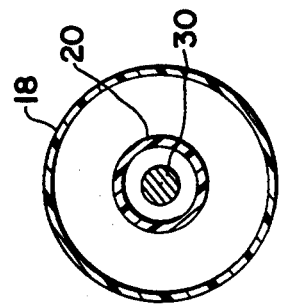
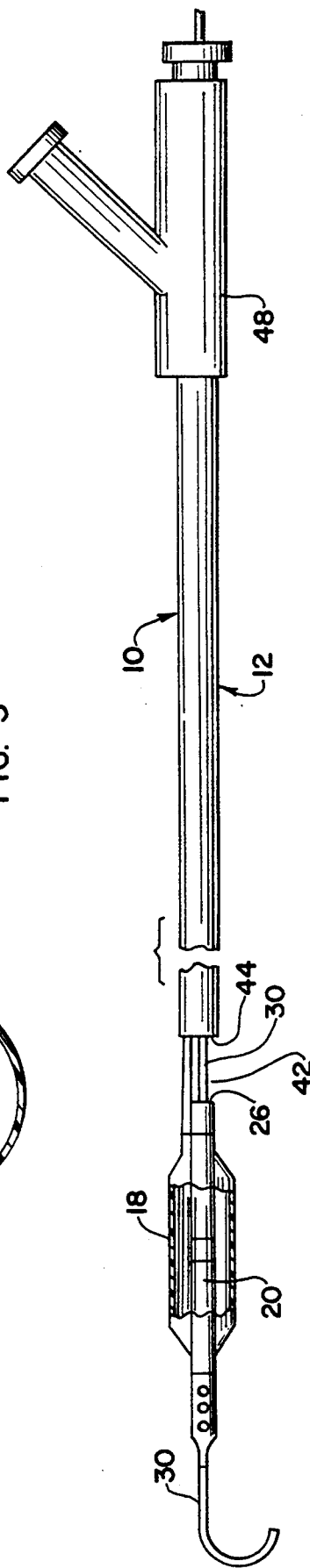

PERFUSION CATHETER WITH MOVING BODY

BACKGROUND OF THE INVENTION

In balloon angioplasty or PTCA, a catheter is advanced through the arterial system of a patient to an area of stenosis where an artery is partially or completely blocked. The catheter, with the balloon deflated, is advanced through the stenotic area, and then the balloon is inflated to expand the stenosis.

With conventional catheters for angioplasty, the blood flow is completely blocked while the balloon is inflated. This tends to limit the amount of time that the inflation of the balloon can be tolerated by the patient.

Thus, in Sahota U.S. Pat. No. 4,581,017; Sogard et al. U.S. Pat. No. 4,944,745 and Horzewski et al. U.S. Pat. No. 4,771,777, among others, balloon catheters for angioplasty are disclosed in which the balloon can be inflated without completely blocking the blood flow through the artery in which the balloon is inflated. However, difficulties may be encountered in prior art designs with respect to the advancement of the guidewire because of the presence of a side aperture proximal to the balloon through which the guidewire may accidentally project during advancement.

In accordance with this invention, an intravascular balloon catheter is provided which addresses the above problem. A guidewire may be reliably advanced through the catheter of this invention without risk of the guidewire projecting laterally out of a proximal side aperture in the catheter, thus becoming stuck and non-advanceable. Additionally, the catheter of this invention can provide a relatively laminar, high volume flow of blood through an inflated balloon in an artery when that is required. At the same time, this flow of blood may be shut off when the guidewire or the catheter are being advanced, and then reopened at any desired time for selective and beneficial clinical advantage.

DESCRIPTION OF THE INVENTION

By this invention, an intravascular balloon catheter is provided which comprises a catheter body portion having a proximal and a distal end, and having a balloon carried adjacent the distal end. The catheter also defines an inflation tube which extends along essentially the length of the catheter proximal to the balloon, and which communicates with the interior of the balloon. The catheter body portion also defines a second lumen having an open, distal end and extending along at least most of the length of the body. A first tube is also provided, being aligned with the second lumen, and extending through the balloon. The first tube is then open at both ends to serve as a route for blood to pass by the inflated balloon.

The catheter body which defines the second lumen is longitudinally slidable relative to the balloon, the first tube, and the inflation tube between an advanced position and a retracted position. In the advanced position, the second lumen and first tube are positioned together, to facilitate the advancement of a guidewire through both the second lumen and the first tube. In the retracted position, the second lumen is spaced from the first tube to provide an opening between them. The first tube is then open to receive blood flow therethrough, while the catheter occupies a blood vessel and the balloon is expanded. This avoids interruption of blood flow through the blood vessel. Typically, the catheter body portion slides back and forth on the inflation tube.

Preferably, the inflation tube may be of kidney or crescent-shaped cross section. Also, the slidable catheter body portion may define another lumen which receives the kidney-shaped inflation tube in generally loosely fitting, slidable relation, with the other lumen being kidney shaped as well. The effect of this is to prevent rotation of the slidable catheter portion about the inflation tube, so that the first tube and the second lumen are always aligned, because of the non-rotating characteristic of the slidable catheter portion on the inflation tube of the catheter body. Generally, the inflation tube and the other lumen may be of any non-circular cross-section to achieve this result.

Since the second lumen receives the guidewire, at least the inner lumen surface of the sleeve will preferably be made of a lubricating material such as PTFE.

DESCRIPTION OF DRAWINGS

In the drawings, FIG. 1 is a plan view of a catheter in accordance with this invention, shown in its advanced position;

FIG. 2 is an enlarged longitudinal sectional view of the distal end of one embodiment of the catheter of this invention, taken along line 2—2 of FIG. 1;

FIG. 3 is a sectional view taken along line 3—3 of FIG. 2;

FIG. 4 is a sectional view taken along line 4—4 of FIG. 1; and

FIG. 5 is a plan view of the catheter of FIG. 1, shown in its retracted position.

DESCRIPTION OF SPECIFIC EMBODIMENTS

Referring to FIGS. 1-5 a catheter 10 is shown, having a sliding catheter body portion 12 which extends most of the length of the catheter, and relatively strong, flexible, but self-supporting inflation tube 14. A proximal catheter hub 16 of conventional design is also provided, plus a distal, tubular catheter balloon 18 which is carried on first or perfusion tube 20, which is also flexible but self-supporting. First tube 20, in turn, has a tapered or drawn down distal tip 22 and side holes 24 positioned distally of the balloon. The proximal end 26 of first tube 20 is open.

Inflation tube 14 is secured at its proximal end to a lumen in hub 16 which communicates with hub arm 28 for providing pressurized fluid for balloon inflation. The distal end of inflation tube 14 communicates with the interior of balloon 18, through a sealed end 29 of balloon 18. The balloon ends may be sealed to first tube 20 in accordance with conventional technology.

A guidewire 30, having a conventional, springed, J-like tip is shown extending through the straight port 32 of catheter hub 16, through second lumen 34 defined in sliding catheter body portion 12, through lumen 35 of first tube 20, and out the distal end 22, as shown. Thus, catheter 10 can be advanced along guidewire 30, for example into the arterial system of a patient for coronary angioplasty (PTCA). Also, a guidewire 30 may be advanced through the emplaced catheter, as may be desired. Balloon 18 is inflatable and deflatable through inflation tube 14, which can be of crescent or kidney shape as shown in FIG. 4. Sliding catheter body portion 12 defines a first lumen 36 through which inflation tube 14 extends in loosely fitting, sliding relationship.

Thus, the double lumen catheter body portion 12 is manually slidable by gripping its proximal end portion 40 and sliding catheter body portion 12 rearwardly from the advanced position shown in FIG. 1 into the retracted position shown in FIG. 5. In the advanced position, guidewire 30 is easily advanced through the catheter. In the retracted position of FIG. 5, proximal end 26 of first tube 20 becomes open, opening first tube 20 to the flow of blood through tube 20 and the balloon even when balloon 18 is inflated within a blood vessel. To further facilitate this, guidewire 30 may be withdrawn so that the guidewire no longer occupies first tube 20, being typically withdrawn proximally beyond the open space 42 created between the distal end 44 of sliding body portion 12 and the proximal end 26 of first tube 20.

Thus, in this latter position, blood can flow with greater freedom through the region of balloon 18 despite the inflation of the balloon. Thus, balloon 18 may be held in inflated condition for a longer period of time for improved angioplasty, while blood can still pass across the balloon 18 to nourish tissues downstream thereof.

If desired, beginning about 27 centimeters from the distal end 22 of the catheter, a longitudinal slit 46 may be defined in the wall of sliding catheter body portion 12, which may be aligned and coaxial with a longitudinal slot 48 defined in hub 16, for rapid exchange of catheter 10 with another catheter without the need for a guidewire extension, in accordance with the teachings of Johnson et al. U.S. Pat. No. 5,205,822 for example, or with other similar rapid exchange catheter techniques.

Thus, a catheter is provided which easily permits a guidewire to advance through a balloon without the disadvantages of prior art systems recited above, in which the catheter can be moved into a configuration where a high volume blood flow with lower turbulence can take place through an inflated balloon, to prolong the possible balloon inflation times in angioplasty procedures.

Sliding outer body portion 12 may be manufactured by extrusion of plastic in accordance with the teachings, for example, of Fontirroche U.S. Pat. No. 5,063,018. Also, tube 14 of crescent or kidney-shaped cross section may have a proximal section of major length which is made of relatively rigid plastic, or plastic fused to a metal sheath of crescent of kidney-shaped cross section. Then, approximately the distal 20 centimeters of inflation tube 14 may be made of a material which is more flexible, for example by terminating the metal portion of the sheath, while a plastic portion of the sheath continues into sealing engagement with balloon 18 to permit inflation thereof. Alternatively, sheath 14 may be made of metal along its entire distance, but of an alloy such as nickel-titanium alloy, which softens permanently on heating, so that the distal tip of the metal sheath can be softened and rendered more flexible.

Because of the open characteristic of space 42, being open on three sides in this embodiment, and the open-ended, tubular characteristic of tube 20, a smooth, more laminar flow of blood can be provided at higher flow rates during balloon inflation episodes. This permits a longer period of balloon inflation without causing ischemia and with less damage to blood cells.

The length of space 42 is preferably no less than the inner diameter of first tube 20, to be sure there is adequate access to flowing blood, to achieve the maximum blood flow that first tube 20 can handle.

The above has been offered for illustrative purposes only, and is not intended to limit the scope of the invention of this application, which is as defined in the claims below.

That which is claimed is:

1. An intravascular balloon catheter, which comprises:
a catheter body portion; a catheter balloon; inflation tube which extends along essentially the length of said catheter proximal to said catheter balloon and which communicates with the interior of said balloon; said catheter body portion defining a guidewire lumen having an open, distal end and extending along said body portion; and
a first tube, aligned with said guidewire lumen, said first tube extending along said balloon and open at both ends, said inflation tube being non-circular in cross section, and said catheter body portion defining another, non-circular lumen receiving said inflation tube in non-rotating slidable relation to permit said catheter body portion to be longitudinally slidable relative to said balloon, said first tube, and said inflation tube between an advanced position in which the guidewire lumen and first tube are together to allow advancement of a guidewire through both said guidewire lumen and first tube, and a retracted position in which the guidewire lumen is spaced from said first tube, whereby said first tube is open to receive blood flow therethrough.

2. The catheter of claim 1 in which said body portion is slidable along said inflation tube.

3. The catheter of claim 1 in which said inflation tube and non-circular lumen are both crescent-shaped in cross section.

4. The catheter of claim 3 in which said balloon is carried by said first tube.

5. The catheter of claim 1 in which said balloon is carried by said first tube.

6. An intravascular balloon catheter, which comprises:
a catheter balloon; an inflation tube which extends proximal to said catheter balloon and which communicates with the interior of said balloon; a catheter body portion which is slidable along said inflation tube, said catheter body portion defining a guidewire lumen having an open, distal end and extending along said body portion; and a first tube, aligned with said guidewire lumen, said first tube carrying said balloon and being open at both ends, said inflation tube being non-circular in cross-section, and said catheter body portion defining another, non-circular lumen receiving said non-circular inflation tube in non-rotating, slidable relation while permitting said catheter body portion to be longitudinally slidable relative to said balloon, said first tube, and said inflation tube between an advanced position in which the guidewire lumen and first tube are together to allow advancement of a guidewire through both said guidewire lumen and said first tube, and a retracted position in which the guidewire lumen is spaced from said first tube, whereby said first tube is open to receive blood flow therethrough.

7. The catheter of claim 6 in which said inflation tube and non-circular lumen are both crescent shaped in cross section.

* * * * *